United States Patent
Inoue et al.

(12)

(10) Patent No.: US 6,420,553 B1
(45) Date of Patent: Jul. 16, 2002

(54) METHOD FOR PREPARING METAL COMPLEX OF PORPHYRIN

(75) Inventors: Yoshihisa Inoue; Victor Borovkov, both of Toyonaka; Juha Lintuluoto, Osaka, all of (JP)

(73) Assignee: Japan Science and Technology Corporation, Saitam (JP)

(*) Notice: Subject to any disclaimer, the term of this patent is extended or adjusted under 35 U.S.C. 154(b) by 0 days.

(21) Appl. No.: 09/646,448

(22) PCT Filed: Mar. 8, 1999

(86) PCT No.: PCT/JP99/01113
§ 371 (c)(1),
(2), (4) Date: Oct. 31, 2000

(87) PCT Pub. No.: WO99/46265
PCT Pub. Date: Sep. 16, 1999

(30) Foreign Application Priority Data

Mar. 9, 1998 (JP) .............................................. 10-57246

(51) Int. Cl.[7] ............................................. C07D 487/22
(52) U.S. Cl. ....................................................... 540/145
(58) Field of Search ......................................... 540/145

(56) References Cited

FOREIGN PATENT DOCUMENTS

JP           4-283580           10/1992

OTHER PUBLICATIONS

Pauling, General Chemistry, 2nd ed,. W. H. Freeman and Company, 1953, 192–211.*
Ono et al, JP 4–283580, abstract.

* cited by examiner

*Primary Examiner*—Richard L. Raymond
*Assistant Examiner*—Kahsay Habte
(74) *Attorney, Agent, or Firm*—Knobbe, Martens, Olson and Bear, LLP

(57) ABSTRACT

A process for producing a metalloporphyrin containing a transition metal inserted into the porphyrin ring which comprises dissolving a porphyrin compound and a transition metal salt each in an independent solvent, combining the solutions, and carrying out the reaction in the presence of a basic substance. By this process a metalloporphyrin containing a transition metal inserted into the porphyrin ring can be synthesized easily under mild conditions and with high selectivity.

6 Claims, No Drawings

METHOD FOR PREPARING METAL COMPLEX OF PORPHYRIN

This application is the U.S. National Phase under 35 U.S.C. §371 of International Application PCT/AP99/01113, filed Mar. 8, 1999, which claims priority based on JP 1998-57246, filed Mar. 9, 1998.

TECHNICAL FIELD

The present invention relates to a process for producing metalloporphyrins. More particularly, the present Invention relates to a process for producing metalloporphyrins containing transition metals inserted into the porphyrin ring which are useful as functional materials, such as photoresponsive materials and organoelectronic materials.

BACKGROUND ART

With regard to porphyrins discovered as substances Involved in photosynthesis, studies are In progress on the structural control, chemical modification, and exploitation thereof as photoresponsive materials or electronic materials.

In the course of these studies, metalloporphyrins containing transition metals inserted into the porphyrin ring are gathering attention.

However, in the production of such porphyrin-metal complexes. the insertion of a transition metal ion into the porphyrin ring has been found to be difficult and because of the high temperature conditions required [a) Meumier et al. Bull. Soc. Chim. Fr. 1994, 131, 78–88. b) Collman et al. J. Am. Chem. Soc 1995, 117, 692–703. c) Ohkubo et al. J. Mol. Cat., 1994, 91, 7–17. d) Guilard et al. J. Am. Chem. Soc. 1994, 116, 10202–10211. e) Meumier et al. Inorg. Chem 1991, 30, 706–711. f) Saveant et al. J. Am. Chem. Soc. 1991, 113, 1586–1595. g) Quici et al. J. al. J. Mol. Cat. A: Chemical 1996, 113, 77–86] and the inert atmosphere required for conducting the reaction [a) Meumier and Momenteau et al. J. Mol. Cat. A: Chemical 1996, 113, 23–34. b) Tsuchida et al. J. Chem. Soc. Dalton Trans. 1990, 2713–2718. c) Collman et al J. Am. Chem. Soc. 1975, 97, 1427–1439. d) Groves et al. J. Am. Chem. Soc. 1983, 105, 5791–5796.], among other restrictions, it has been impossible to synthesize transition metal-porphyrin complexes easily under mild conditions using transition metals and porphyrins in desired combinations.

Therefore, an object of the present invention Is to solve the problem of those prior arts and to provide a novel technology for producing metalloporphyrins by which a transition metal ion can be inserted into the porphyrin ring of an arbitrary hydrophobic or hydrophilic porphyrin compound expediently with high selectivity, for example by conducting the necessary reaction at room temperature.

DISCLOSURE OF INVENTION

Accomplished in the above state of the art, the present invention is directed, in a first aspect thereof, to a process for producing a metalloporphyrin containing a transition metal inserted into the porphyrin ring which comprises dissolving a porphyrin compound and a transition metal salt each in an independent solvent, combining the two solutions, and reacting them in the presence of a basic substance or basic substances.

In connection with this first aspect, the present invention provides, in a second aspect thereof, a process for producing a metalloporphyrin wherein the basic substance is supplied in the form of the solvent for dissolving the porphyrin compound; in a third aspect, a process for producing a metalloporphyrin wherein the basic substance is added at the stage of mixing the solutions; in a fourth aspect, a process for producing a metalloporphyrin wherein said reaction is carried out at a temperature not over 40° C.; in a fifth aspect, a process for producing a metalloporphyrin wherein the transition metal salt is an inorganic salt of iron (Fe) or manganese (Mn); and in a sixth aspect, a process for producing a metalloporphyrin wherein the porphyrin is an optionally substituted hydrophobic or hydrophilic porphyrin compound.

BEST MODE FOR CARRYING OUT THE INVENTION

While the present invention has the above features, its technical essence lies in enabling synthesis of various metalloporphyrins in a homogeneous reaction system under mild conditions and with high selectivity.

The working modes of the present invention are now described.

First, in the process for producing a metalloporphyrin according to the present invention, hydrophobic or hydrophilic porphyrin compounds having a porphyrin ring or rings and optionally bearing various substituent groups can be used as starting materials. These starting materials have structures permitting insertion of a transition metal ion.

The fundamental structure involved may be visualized as having a porphyrin ring of the following formula:

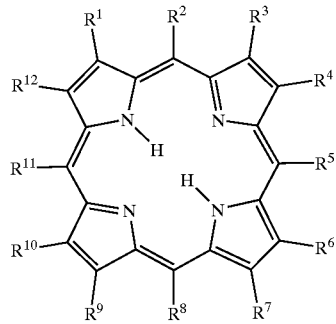

(wherein $R^1$~$R^{12}$ each represents a hydrogen atom or an organic group).

As examples of said organic group for $R^1$~$R^{12}$, there can be mentioned hydrocarbon groups, whether acyclic or cyclic and whether saturated or unsaturated, such as alkyl, alkenyl, cycloalkyl, phenyl, naphthyl, etc., which may optionally be substituted by various functional groups such as halogen, hydroxy, alkoxy, alkoxycarbonyl, carboxy, amido, amino, nitro, cyano, carbamate, urea, sulfonyl, sulfenyl, phosphenyl, phosphinyl, sulfide, thioether, thioester, etc.; heterocyclic groups such as pyridyl, piperidyl, azino, azolyl, imidazolyl, triazinyl, furyl, carbazolyl, etc.; organic groups having a sugar moiety or a cyclodextrin or porphyrin ring.

Furthermore, $R^1$~$R^{12}$, between adjacent ones, may form a heterocycle or a carbocycle with or without the intermediary of a heteroatom or heteroatoms. The transition metal salts to be complexed with such porphyrin compounds may be any of various salts of transition metals that are able to make at least two formal bonds. Thus, the transition metal includes but is not limited to Fe, Ni, Co, Cu, Zn, Ti, Mn, Mo, V, Zr, Cd, Sb, Cr, and Nb. As far as the present invention is concerned, Fe (iron) and Mn (manganese) can be mentioned as preferred transition metals.

The salt of such a transition metal may be any of various inorganic acids, such as hydrochloric acid, sulfuric acid, phosphoric acid, etc., and various organic acids. Particularly preferred are salts of inorganic acids, such as $FeCl_2$ and $MnCl_2$.

In the process according to the present invention, said transition metal salt is preferably used in a molar excess over the starting material porphyrin. The molar ratio may for example be 1.1~30, more preferably 2~25, and still more preferably 5~20.

In conducting the reaction, the starting material porphyrin and the transition metal salt are dissolved each in an independent solvent and the resulting solutions are combined. This procedure of dissolving the porphyrin and the transition metal salt in independent solvents and combining the solutions is an indispensable requisite in carrying out the process of the present invention.

The solvent for dissolving the starting material porphyrin can be generally selected according to whether the particular porphyrin is hydrophobic or hydrophilic. Moreover, a solvent having a high solubilizing power for the porphyrin and capable of providing a homogeneous solution is selected. Taking a hydrophobic porphyrin as an example, hydrophobic organic solvents are selectively used. Thus, halogenated hydrocarbons, aromatic hydrocarbons, nitriles, etc. may be mentioned. In particular, halogenated hydrocarbons such as chloroform ($CHCl_3$), dichloromethane ($CH_2Cl_2$), etc. constitute a preferred class of organic solvents.

On the other hand, when the starting material porphyrin is hydrophilic, hydrophilic solvents such as water, alcohols, amines, nitrogeneous heterocyclic compounds, etc. can be generally employed.

The homogeneous solutions thus prepared are combined. In this combined solution, a basic substance or basic compound is caused to be present. This presence of a basic substance can be assured, for example by using a basic substance as the solvent when it is an amine or a nitrogeneous heterocyclic compound or by adding a basic substance to the combined solution, or even by using such procedures in combination.

The relative amount of the solvent and basic substance is not particularly restricted but can be freely selected within the range assisting in the transition metal insertion reaction according to the invention and not adversely affecting the process.

The basic substance which can be used includes nitrogen-containing heterocyclic compounds such as pyridine, methylpyridine, dimethylpyridine, diazines, methyldiazines, pyrazine, ethylpyrazine, pyrimidine, piperazine, morpholine, etc.; aliphatic amines such as diethylamine, ethylenediamine, tert-butylamine, etc.; basic resins; and inorganic bases.

In particular, organic basic substances such as 2,6-lutidine are preferred.

The reaction temperature may generally be not over 40° C. This limit of 40° C. may at times be exceeded but It does not happen that this limit is exceeded in any remarkable measure. Actually, the reaction can be conducted at room temperature or in the neighborhood thereof. In this respect, the process of the invention is basically different from the conventional processes.

After completion of the reaction, the reaction product can be isolated and purified by various procedures such as chromatography, precipitation, recrystallization, etc.

The following examples Illustrate the present invention in further detail.

EXAMPLES

<A> In the following examples, the porphyrin compounds identified below were used as starting materials to synthesize the corresponding transition metal-porphyrine complexes.

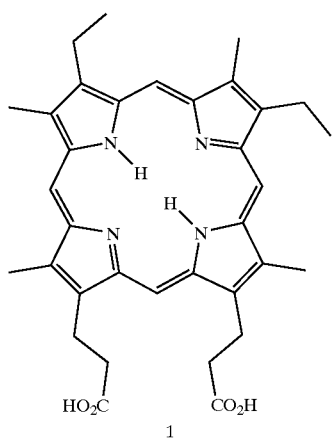

1

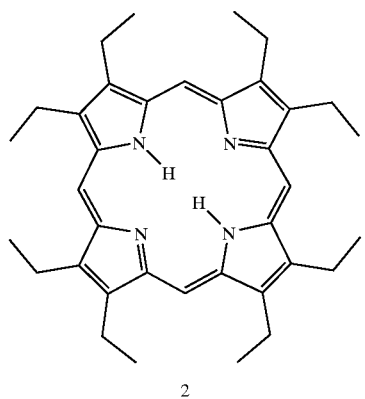

2

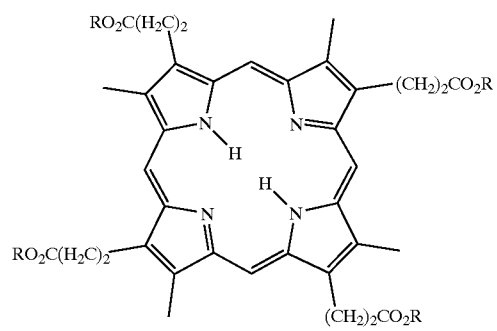

3 R = H
4 R = Me

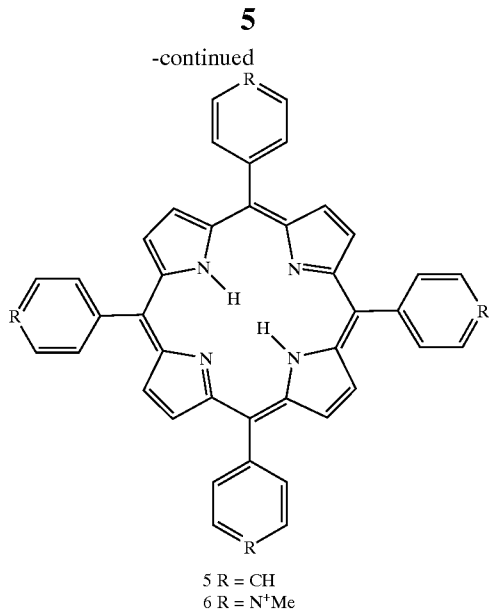

5 R = CH
6 R = N⁺Me

Example 1

The hydrophobic octaethylporphyrin of the above formula (2) (16 μmol) was dissolved in chloroform (5 ml). Separately, $FeCl_2$ (260 μmol; 16 molar equivalents based on said octaethylporphyrin) was dissolved in methanol (3 ml).

The solution of octaethylporphyrin in chloroform and the solution of $FeCl_2$ in methanol were combined and a few drops of 2,6-lutidine was added.

The mixture was stirred at room temperature for 3 hours.

As a result, Fe was inserted into the porphyrin ring to give octaethylporphyrin-Fe complex in quantitative (100%) yield.

Example 2

Using $MnCl_2$ in lieu of $FeCl_2$, the procedure of Example 1 was otherwise followed. Here, the reaction was carried out at room temperature for 7 hours. As a result, Mn was inserted into the porphyrin ring to give octaethylporphyrin-Mn complex also in quantitative yield.

Example 3

In lieu of the octaethylporphyrin used in Example 1, the porphyrin tetramethyl ester shown above was used. This ester was dissolved in chloroform (10 ml) and the reaction was carried out under the same conditions as in Example 1.

As a result, Fe was inserted into the porphyrin ring to give coproporphyrin tetramethyl ester-Fe complex in quantitative yield.

Example 4

$MnCl_2$ in lieu of the $FeCl_2$ was used and the reaction was carried out at room temperature for 7 hours. The procedure of Example 3 was otherwise repeated.

As a result, coproporphyrin tetramethyl ester-Mn complex was similarly obtained.

Example 5

The hydrophilic coproporphyrin of the above formula (3) (16 mmol) was dissolved in 2,6-lutidine (5 ml). On the other hand, $FeCl_2$ (260 μmol) was dissolved in methanol.

The above lutidine solution and $FeCl_2$ methanolic solution were combined and stirred at room temperature for 7 hours.

As a result, Fe was inserted into the porphyrin ring to give coproporphyrin-Fe complex in quantitative yield.

Example 6

Using $MnCl_2$ in lieu of $FeCl_2$, the procedure of Example 5 was otherwise repeated. This reaction was carried out under stirring at room temperature for 20 hours.

As a result, Mn was inserted into the porphyrin ring to give coproporphyrin-Mn complex in quantitative yield.

Example 7

Using the hydrophilic mesoporphyrin IX of the above formula (1) in lieu of coproporphyrin, the procedure of Example was otherwise repeated.

As a result, Fe was inserted into the porphyrin ring to give mesoporphyrin IX-Fe complex in quantitative yield.

Example 8

Using $MnCl_2$ in lieu of $FeCl_2$, the procedure of Example 7 was otherwise followed. Here, the reaction was carried out under stirring at room temperature for 20 hours.

As a result, Mn was inserted into the porphyrin ring to give mesoporphyrin IX-Mn complex in quantitative yield.

Example 9

The hydrophobic tetraphenylporphyrin of the above formula (5) (16 μmol) was dissolved in chloroform (10 ml). On the other hand, $MnCl_2$ (260 μmol) was dissolved in methanol.

The chloroform solution and the $MnCl_2$ methanolic solution were combined and a few drops of 2,6-lutidine was added.

The mixed solution was stirred at room temperature for 48 hours. As a result, Mn was inserted into the porphyrin ring to give tetraphenylporphyrin-Mn complex in quantitative yield.

Example 10

The hydrophilic tetra(N-methylpyridyl)porphyrin of the above formula (6) (16 μmol) was dissolved in water (5 ml). On the other hand, $MnCl_2$ (260 μmol) was dissolved in methanol (3 mol).

The above aqueous solution and $MnCl_2$ methanolic solution were combined and a few drops of 2,6-lutidine was added.

The mixture was stirred at room temperature for 24 hours.

As a result, Mn was inserted into the porphyrin ring to give tetra(N-methylpyridyl)porphyrin-Mn complex in quantitative yield.

<B> In the following examples, the dimerized porphyrin containing Zn inserted into one of the porphyrin rings as depicted below was used as the starting material.

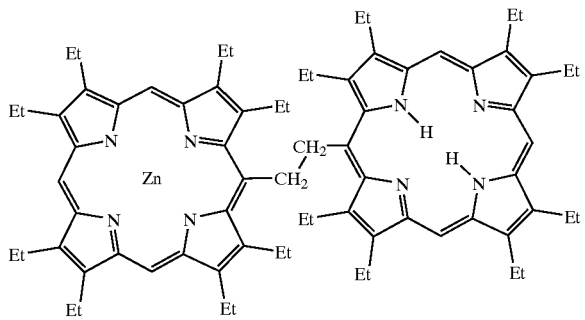 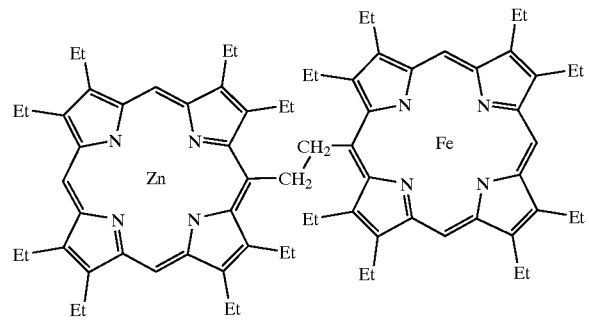

Example 11

The above porphyrin dimer-Zn complex was dissolved in chloroform. On the other hand, 16 molar equivalents of $MnCl_2$ was dissolved in methanol.

The two solutions were mixed and a few drops of 2,6-lutidine was added.

The reaction was conducted under stirring at room temperature for about 1 hour.

As a result, Mn was inserted into the other porphyrin ring to give porphyrin heterodimer-Zn/Mn complex of the following formula in quantitative yield.

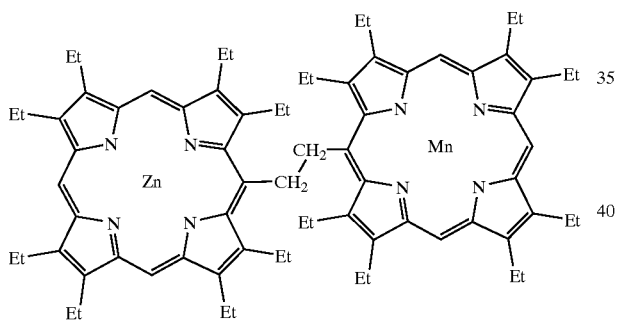

The characteristic values of this compound are as follows.

TABLE 1

UV-vis ($CHCl_3$) $\lambda_{max}$ (log ε) 589 (4.15), 581 (4.16), 552 (4.19), 485 (4.66), 417 (Soret, 5.24), 370 nm (4.92); FAB-MS (NBA) m/z 1216 ([M + 6]$^+$, 11%), 1215 ([M + 5]$^+$, 27), 1214 ([M + 4]$^+$, 44), 1213 ([M + 3]$^+$, 48), 1212 ([M + 2]$^+$, 63), 1211 ([M + 1]$^+$, 63), 1210 (M$^+$, 70), 1209 ([M − 1]$^+$, 13), 613 ([M-MnOEPCH$_2$ + 3]$^+$, 37), 612 ([M-MnOEPCH$_2$ + 2]$^+$, 31), 611 ([M-MnOEPCH$_2$ + 1]$^+$, 49), 610 ([M-MnOEPCH$_2$]$^+$, 35), 609 ([M-MnOEPCH2 − 1)$^+$, 67), 601 ([M-ZnOEPCH$_2$ + 1]$^+$, 51), 600 ([M-ZnOEPCH$_2$]$^+$, 100), 599 ([M-ZnOEPCH$_2$ − 1]$^+$, 44), 598 ([M-ZnOEPCH$_2$ − 2]$^+$, 26).

Example 12

Using $FeCl_2$ in lieu of $MnCl_2$, the procedure of Example 11 was otherwise repeated. As a result, Fe was inserted into the porphyrin ring to give porphyrin heterodimer-Zn/Fe complex of the following formula in a yield of 45%.

As a byproduct, the Fe/Fe complex containing Fe inserted into both porphyrin rings was also formed (25%).

The characteristic values of the above porphyrin heterodimer-Zn/Fe complex were as follows.

TABLE 2

UV-vis ($CHCl_3$) $\lambda_{max}$ (log ε) 592 (4.21), 578 (4.19), 551 (4.31), 418 (Soret, 5.34), 363 sh nm (4.77), FAB-MS (NBA) m/z 1216 ([M + 5]$^+$, 7%), 1215 ([M + 4]$^+$, 11), 1214 ([M + 3]$^+$, 13), 1213 ([M + 2]$^+$, 16), 1212 ([M + 1]$^+$, 17), 1211 (M$^+$, 16), 1210 ([M − 1]$^+$, 7), 615 ([M-FeOEPCH$_2$ + 5]$^+$, 15), 614 ([M-FeOEPCH$_2$ + 4]$^+$, 21), 613 ((M-FeOEPCH$_2$ + 3]$^+$, 43), 612 ((M-FeOEPCH$_2$ + 2]$^+$, 34), 611 ([M-FeOEPCH$_2$ + 1]$^+$, 57), 610 ([M-FeOEPCH$_2$]$^+$, 42), 609 ([M-FeOEPCH$_2$ − 1]$^+$, 80), 606 ([M-FeOEPCH$_2$ − 2]$^+$, 17), 607 ([M-FeOEPCH$_2$ − 3]$^+$, 16), 603 ([M-ZnOEPCH$_2$ + 2]$^+$, 15), 602 ([M-ZnOEPCH$_2$ + 1]$^+$, 46), 601 ([M-ZnOEPCH$_2$]$^+$, 100), 600 ([M-ZnOEPCH$_2$ − 1]$^+$, 30), 599 ([M-ZnOEPCH$_2$ − 2]$^+$, 32) 598 ([M-ZnOEPCH$_2$ − 3]$^+$, 14), 597 ([M-ZnOEPCH$_2$ − 4]$^+$, 16).

INDUSTRIAL APPLICABILITY

As described above in detail, metalloporphyrins containing transition metals inserted into the porphyrin ring can be synthesized easily under mild conditions and with high selectivity in accordance with the present invention.

What is claimed is:

1. A process for metallating a porphyrin having the structure:

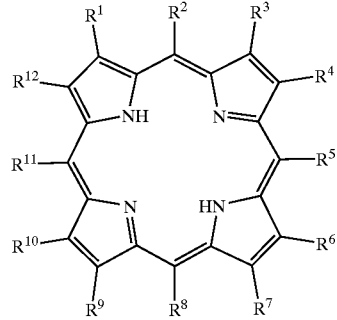

wherein $R^1$–$R^{12}$ is selected from the group consisting of a hydrogen atom, hydrocarbon group, and heterocyclic group; said hydrocarbon group is selected from the group consisting of alkyl, alkenyl, cycloalkyl, phenyl, and naphthyl which may optionally be substituted by at least one functional group selected from the group consisting of halogen, hydroxy, alkoxy, alkoxycarbonyl, carboxy, amido, amino, nitro, cyano, carbamate, urea, sulfonyl, sulfenyl, phosphenyl, phosphinyl, sulfide, thioether, thioester, sugar moiety, cyclodextrin, and porphyrin ring;

said heterocyclic group is selected from the group consisting of pyridyl, piperidyl, azino, azolyl, imidazolyl, triazinyl, furyl and carbozoyl;

said $R^1$–$R^{12}$, between adjacent ones, may form a heterocycle or a carbocycle with or without the intermediary of hetero atom or hetero atoms; comprising the steps of:

dissolving the porphyrin in a solvent to form a first solution;

dissolving a transition metal salt in a solvent to form a second solution;

combining the first solution with the second solution to form a third homogenous solution,
wherein the transition metal salt is in molar excess over the porphyrin; and carrying out a reaction in the third solution in the presence of a basic substance at a temperature not exceeding 40° C.; thereby producing a metalloporphyrin from said porphyrin.

2. The process of metallating a porphyrin according to claim 1, wherein said basic substance is present in the reaction as the solvent for said porphyrin compound.

3. The process of metallating a porphyrin according to claim 1, wherein the basic substance is present in the reaction by addition when the first solution and second solution are combined.

4. The process of metallating a porphyrin according to claim 1 wherein said transition metal salt is an inorganic salt of iron (Fe) or manganese (Mn).

5. The process of metallating a porphyrin according to claim 1, wherein said porphyrin compound is a substituted hydrophobic porphyrin compound.

6. The process of metallating a porphyrin according to claim 1, wherein said porphyrin compound is a substituted hydrophilic porphyrin compound.

* * * * *